United States Patent [19]

Gandolfi et al.

[11] 4,285,966

[45] Aug. 25, 1981

[54] CERTAIN 15-EPI-PROSTACYCLINS

[75] Inventors: Carmelo Gandolfi, Milan; Carlo Passarotti, Gallarate; Alessandro Andreoni, Cologno Monzese; Angelo Fumagalli, Monza; Franco Faustini; Roberto Cesarani, both of Milan, all of Italy

[73] Assignee: Farmitalia Carlo Erba, S.p.A., Milan, Italy

[21] Appl. No.: 955,631

[22] Filed: Oct. 30, 1978

[30] Foreign Application Priority Data

Nov. 25, 1977 [IT]  Italy ................................ 30029 A77

[51] Int. Cl.³ ................ C07D 307/935; A61K 31/557
[52] U.S. Cl. .................................... 424/285; 424/283; 542/421; 542/426; 542/429; 542/430; 542/431; 260/345.7 R; 260/345.8 R; 260/345.2; 260/346.22; 260/346.73; 544/376; 546/269; 548/236; 549/60
[58] Field of Search ...................... 260/346.22, 346.73, 260/308; 542/421, 426, 429, 430

[56] References Cited

U.S. PATENT DOCUMENTS 4,158,667  6/1979  Axen .................................... 260/413

FOREIGN PATENT DOCUMENTS 851122  8/1977  Belgium .
864644  9/1977  Belgium .
854463  11/1977  Belgium .
867836  10/1978  Belgium .

OTHER PUBLICATIONS

Chemical Substance Index, Chem. Abstracts, p. 32919cs, 1972–1976.
Nicolaou et al., J.C.S. Chem. Comm. (1978), pp. 1067–1068.

Primary Examiner—Henry R. Jiles
Assistant Examiner—Bernard Dentz
Attorney, Agent, or Firm—Murray and Whisenhunt

[57] ABSTRACT

The present invention relates to 15-epi-derivatives of prostacyclin and its analogs, to a process for their preparation and to pharmaceutical and veterinary compositions containing them.

12 Claims, 1 Drawing Figure

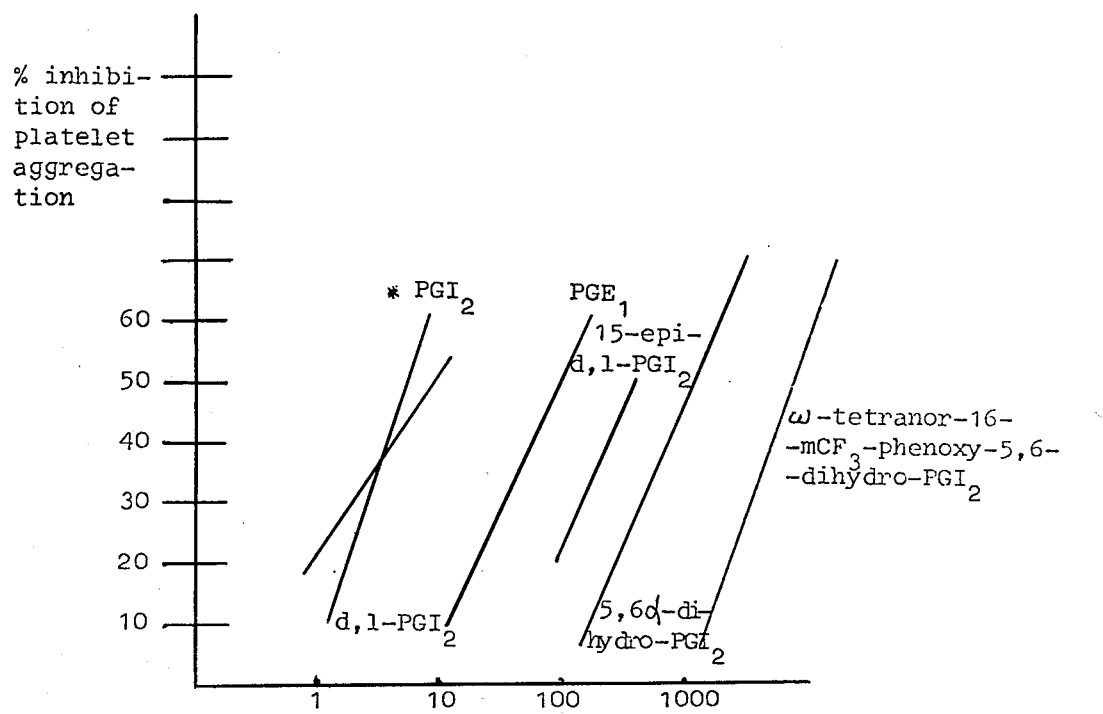

CERTAIN 15-EPI-PROSTACYCLINS

The present invention relates to 15-epi-derivatives of 9-deoxy-6,9α-epoxy-Δ[5]-PGF$_{1α}$ (prostacyclin or PGI$_2$) and analogous prostacyclins, to a process for their preparation and to pharmaceutical and veterinary compositions containing them.

The compounds covered by this invention are bicyclic Prostaglandins of formula (I)

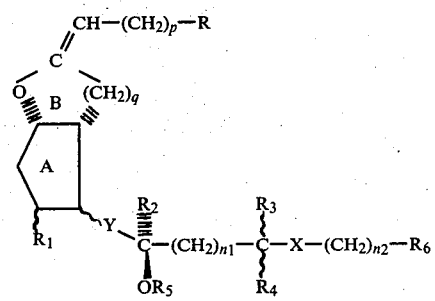

wherein

R is a substituent chosen from the following: (a) —COOR' wherein R' is hydrogen or C$_1$-C$_6$ alkyl; (b) —CH$_2$OH; (c)

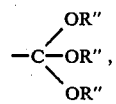

in which the R" groups, whether the same or different, are C$_1$-C$_6$ alkyl or phenyl; (d)

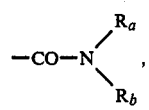

in which R$_a$ and R$_b$ are independently chosen from hydrogen, C$_1$-C$_6$ alkyl, C$_2$-C$_6$ alkanoyl and phenyl; (e) a

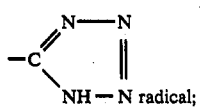

(f) —C≡N;
p is zero or an integer between 1 and 7;
q is 1 or 2;
R$_1$ is hydrogen, hydroxy, C$_1$-C$_6$ alkoxy, aryl-C$_1$-C$_6$-alkoxy, acyloxy;
Y is chosen from the group: —CH$_2$—CH$_2$—, —C≡C—,

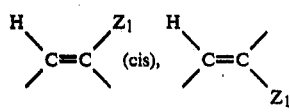

(trans) where Z$_1$ is hydrogen or halogen;
R$_2$ is hydrogen, C$_1$-C$_6$ alkyl, C$_2$-C$_6$-alkenyl, C$_2$-C$_6$ alkynyl, aryl;

R$_5$ is hydrogen, C$_1$-C$_6$ alkyl, aryl-C$_1$-C$_6$-alkyl;
n$_1$ and n$_2$, whether the same or different, are zero or an integer between 1 and 6;
R$_3$ and R$_4$, whether the same or different, may be hydrogen, C$_1$-C$_6$ alkyl or fluorine, or may form a

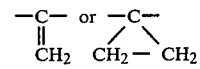

group with a carbon atom to which they are bound;
X is chosen from —O—, —S— and —(CH$_2$)$_m$ wherein m is zero or 1;
R$_6$ is a substituent chosen from (a') hydrogen, (b') C$_1$-C$_4$ alkyl; (c') a cycloaliphatic radical, optionally substituted with one or more C$_1$-C$_6$ alkyl and C$_1$-C$_6$ alkoxy groups; (d') an aryl group optionally substituted with one or more halogen, C$_1$-C$_6$ alkyl, halo-C$_1$-C$_6$-alkyl or C$_1$-C$_6$-alkoxy; (e') a saturated or unsaturated heterocyclic radical optionally substituted with one or more halogen, C$_1$-C$_6$ alkyl, C$_1$-C$_6$ alkoxy, or halo-C$_1$-C$_6$-alkyl.

This invention also includes pharmaceutically and veterinarily acceptable salts of compounds with formula (I), as well as the optical antipodes (the enantiomers), racemic mixtures of the optical antipodes, geometric isomers and their mixtures, and mixtures of diastereomers.

In this discussion, dashed lines ('''') refer to a substituent on a ring in the α (or endo) configuration or to a substituent in the S configuration on a chain. On the other hand, a wedge (—) indicates that a ring substituent is β (or exo) or that a chain substituent is R. A wavy line (∿) implies that the substituent may be in both the α (endo) or β (exo) configuration if on a ring, or in the S or R form if on a chain. In formula (I), the two bonds in the heterocyclic ring B drawn with dashed lines ('''') are cis to one another, while the side chain bound to the cyclopentane ring A is trans to heterocyclic ring B.

Compounds of the invention are both the isomers of formula (I) wherein the double bond exocyclic to heterocycle B is in Z (cis) or in E (trans) configuration and the mixtures of said isomers. In the natural series' compounds (natderivatives), this exocyclic double bond preferably is Z; while in the corresponding enantio derivatives (entderivatives), preferably it is E.

The alkyl, alkenyl, alkynyl, alkoxy and alkanoyl groups may be straight or branched chains.

R is preferably a —COOH group.

The C$_1$-C$_6$ alkyl group is preferably methyl, ethyl or propyl.

The C$_2$-C$_6$ alkanoyl is preferably acetyl or propionyl.

The C$_1$-C$_6$ alkoxy is preferably methoxy, ethoxy or propoxy.

The C$_2$-C$_6$ alkenyl is preferably vinyl, allyl or propenyl.

The C$_2$-C$_6$ alkynyl is preferably ethynyl.

The aryl group is preferably phenyl, tolyl, α-naphthyl or β-naphthyl.

A phenyl group may be unsubstituted or substituted with one or more substituents chosen from C$_1$-C$_6$ alkyl, C$_1$-C$_6$ alkoxy, halo-C$_1$-C$_6$ alkyl and halogen.

An aryl-C$_1$-C$_6$-alkyl group is preferably benzyl and an aryl-C$_1$-C$_6$-alkoxy is preferably benzyloxy.

A halo-C$_1$-C$_6$-alkyl is preferably trihalo-C$_1$-C$_6$-alkyl, particularly trifluoromethyl and trichloromethyl.

An acyloxy group is preferably alkanoyl-oxy, particularly acetoxy or propionyloxy, or benzoyloxy.

When $Z_1$ is halogen, chlorine, bromine or iodine is preferred.

Preferably, $R_3$ and $R_4$ are independently chosen from hydrogen, $C_1$-$C_6$-alkyl and fluorine.

$n_1$ is preferably zero or an integer between 1 and 3; $n_2$ is preferably an integer between 1 and 3.

When $R_6$ is $C_1$-$C_4$ alkyl, methyl is preferred. When $R_6$ is a cycloaliphatic radical, it may be mono-, bi- or tri-cyclic. If monocyclic, a $C_3$-$C_9$ cycloalkyl or cycloalkenyl is preferred, particularly cyclopentyl, cyclohexenyl, cycloheptyl, cyclopentenyl or cycloheptenyl. When $R_6$ is bicyclic or tricyclic, norbornyl or adamantyl groups are preferred, respectively.

If $R_6$ is a cycloaliphatic group, it is preferably a monocyclic cycloalkyl, like cyclohexyl.

When $R_6$ is a heterocyclic radical, this may be mono- or bi-cyclic and contains at least one heteroatom chosen from the group O, S, N. Examples of preferred heteromonocyclic radicals include tetrahydrofuryl, furyl, tetrahydrothienyl, thienyl, tetrahydropyranyl, pyrrolyl, pyrazolyl, oxazolyl, isoxazolyl, pyridyl, pyrazinyl, pyrimidinyl, pyridazinyl. Preferred heterocicyclic radicals include 2-oxa and 2-thiobicyclo[3.3.0]octyl, 2-oxa and 2-thio-bicyclo[3.4.0]nonyl, as well as their aromatic analogues.

Pharmaceutically or veterinarily acceptable salts of compounds (I) are preferbly formed with both inorganic and organic bases.

As examples, acceptable inorganic bases are alkali, e.g. sodium or potassium; alkaline earth, e.g. calcium, zinc or aluminium hydroxides. Acceptable organic bases include organic amines like methylamine, diethylamine, trimethylamine, triethylamine, ethylamine, dibutylamine, triisopropylamine, N-methyl-hexylamine, decylamine, dodecylamine, allylamine, crotylamine, dicyclopentylamine, dicyclohexylamine, benzylamine, dibenzylamine, $\alpha$-phenylethylamine, $\beta$-phenylethylamine, ethylenediamine, diethylenetriamine, as well as similar aliphatic cycloaliphatic, aromatic or heterocyclic amines like piperidine, morpholine, pyrrolidine, piperazine. Substituted derivatives of the latter like 1-methylpiperidine, 4-ethylmorpholine, 1-isopropylpyrrolidine, 2-methylpyrrolidine, 1,4-dimethylpiperazine, 2-methylpiperidine or amines containing hydrophilic groups like mono-, di- and tri-ethanol amine, 2-amino-1-butanol, 2-amino-2-ethyl-1,3-butylethanolamine, 2-amino-2-ethyl-1,3-propanediol, 2-amino-2-methyl-1-propanol, tris-(hdyroxymethyl)-aminomethane, N-phenyl-ethanolamine, N-(p-tert-amylphenyl)-diethanolamine, ephedrine, procain may also be acceptably used.

According to this invention, preferred salts of compound (I) are those in which R is a —$COOR_d$ group where $R_d$ is a pharmaceutically or veterinarily acceptable cation derived from one of the bases mentioned above. Preferred compounds of the invention are the compounds of formula (I) wherein R is —COOR′, wherein R′ is as defined above or

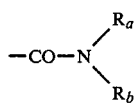

wherein $R_a$ and $R_b$ are as defined above; Y is cis or trans —CH=CH— or —C≡C—; p, q, $R_1$, $R_2$, $R_5$, $n_1$, $n_2$, $R_3$, $R_4$, X and $R_6$ are as defined above, as well as the pharmaceutical or veterinary acceptable salts thereof. Particularly preferred compounds of the invention are the compounds of formula (I) wherein R is —COOR′, wherein R′ is hydrogen or $C_1$-$C_6$ alkyl; p is an integer of 1 to 5; q is 1 or 2; Y is trans —CH=CH— or —C≡C—; $R_1$ is hydrogen or hydroxy; $R_2$ is hydrogen or $C_1$-$C_6$ alkyl; $R_5$ is hydrogen or $C_1$-$C_6$ alkyl; $n_1$ and $n_2$ are, independently, zero or an integer of 1 to 3; $R_3$ and $R_4$ are, independently, hydrogen, $C_1$-$C_6$ alkyl or fluorine; X is —O— or —$(CH_2)_m$— wherein m is zero or 1; $R_6$ is a substituent chosen from (a′) hydrogen; (b′) $C_1$-$C_4$ alkyl; (c′) a monocyclic $C_3$-$C_9$ cycloaliphatic radical optionally substituted with one or more $C_1$-$C_6$ alkyl and $C_1$-$C_6$ alkoxy groups; (d′) a phenyl group optionally substituted with one or more halogen, trihalo-$C_1$-$C_6$-alkyl, $C_1$-$C_6$ alkyl and $C_1$-$C_6$ alkoxy, as well as the pharmaceutical or veterinary acceptable salts thereof. More particularly preferred compounds of the invention are the compounds of formula (I) wherein R is —COOR′, wherein R′ is hydrogen or $C_1$-$C_6$ alkyl; p is 3; q is 1; $R_1$ is hydrogen or hydroxyl; Y is trans -CH=CH- or -C≡C-, preferably —C≡C—; $R_2$ is hydrogen or $C_1$-$C_6$ alkyl; $R_5$ is hydrogen or $C_1$-$C_6$ alkyl; $n_1$ is zero or 1; $R_3$ and $R_4$ are, independently, hydrogen, methyl or fluorine; X is —O— or —$(CH_2)_m$— wherein m is zero or 1; $n_2$ is zero or an integer of 1 to 3; $R_6$ is hydrogen or $C_1$-$C_4$ alkyl, as well as the pharmaceutical or veterinary acceptable salts thereof.

Examples of compounds preferred under this invention are:

d,l-15-epi-$PGI_2$;
nat-15-epi-$PGI_2$;
ent-15-epi-$PGI_2$;
nat-11,15-diepi-$PGI_2$;
ent-11,15-diepi-$PGI_2$;
and the compounds listed below both in the d,l forms and as individual nat- and enantic-isomers:
15-epi-13,14-dehydro-$PGI_2$;
15-epi-20-methyl-$PGI_2$;
15-epi-20-methyl-13,14-dehydro-$PGI_2$;
15-epi-16S,20-dimethyl-$PGI_2$;
15-epi-16R,20-dimethyl-$PGI_2$;
15-epi-20-ethyl-$PGI_2$;
15-epi-16S-methyl-$PGI_2$;
15-epi-16S-methyl-13,14-dehydro-$PGI_2$;
15-epi-16R-methyl-$PGI_2$;
15-epi-16,16-dimethyl-$PGI_2$;
15-epi-17-oxa-$PGI_2$;
15-epi-17-oxa-20-methyl-$PGI_2$;
15-epi-17-trinor-17-(2′-tetrahydrofuryl)-$PGI_2$;
15-epi-17-trinor-17-(2′-furyl)-$PGI_2$;
15-epi-17-trinor-17-phenyl-$PGI_2$;
15-epi-17-trinor-17-cyclohexyl-$PGI_2$;
15-epi-17-trinor-17-cyclopentyl-$PGI_2$;
15-epi-16-tetranor-16-m-trifluoromethylphenoxy-$PGI_2$;
15-epi-16-tetranor-16-p-fluorophenoxy-$PGI_2$;
15-epi-16-tetranor-16-phenyl-$PGI_2$;
15-epi-16-tetranor-16-cyclohexyl-$PGI_2$;
15-epi-16-tetranor-16-(2′-norbornyl)-$PGI_2$;
15-epi-13,14-dihydro-$PGI_2$;
15-epi-13,14-dehydro-16(R) or (S,R)-methyl-$PGI_2$;
15-epi-16(S),(R) or (S,R)-fluoro-$PGI_2$;
15-epi-17-trinor-16-methyl-16-butoxy-$PGI_2$;
15-epi-17-trinor-16-methyl-16-propoxy-$PGI_2$;
15-epi-17-trinor-16-methyl-16-amyloxy-$PGI_2$;
15-epi-17-trinor-16(S),(R) or (S,R)-fluoro-17-cyclohexyl-$PGI_2$;

15-epi-17-trinor-13,14-dehydro-17-cyclohexyl-PGI$_2$;
15-epi-17-trinor-13,14-dehydro-17-phenyl-PGI$_2$;
15-epi-17-trinor-13,14-dehydro-16(S),(R) or (S,R)-fluoro-17-cyclohexyl-PGI$_2$;
15-epi-16-tetranor-16-m-chlorophenoxy-PGI$_2$;
15-epi-16-tetranor-16-p-chlorophenoxy-PGI$_2$;
15-epi-16-tetranor-16-butoxy-PGI$_2$;
15-epi-11-deoxy-PGI$_2$;
15-epi-11-deoxy-16S-methyl-13,14-dehydro-PGI$_2$;
15-epi-11-deoxy-16S-methyl-PGI$_2$;
15-epi-11-deoxy-16,16-dimethyl-17-oxa-PGI$_2$;
15-epi-11-deoxy-16,16,20-trimethyl-17-oxa-PGI$_2$;
15-epi-11-deoxy-16,16-dimethyl-20-ethyl-17-oxa-PGI$_2$;
and the corresponding 11,15-diepi derivatives as well as the pharmaceutical or veterinary acceptable salts of all the compounds listed above.

Belgian Pat. No. 851,122 (Derwent-Farmdoc number 57511 Y) describes 9-oxides-6,9α-epoxy-Δ$^5$-PGF$_{1α}$. In addition to other effects, it inhibits platelet aggregation and prevents thrombus formation while acting as a hypotensive vasodilatory.

This Belgian patent also reports that the best biological response in terms of the specificity, potency and duration of effect is seen with the 15S-hydroxy-9-oxide-6,9α-epoxy-Δ$^5$-PGI$_{1α}$ derivatives, which are almost the only compounds described in the patent. This is consistent with several literature reports that 15-epi or 15R-hydroxy derivatives are generally less active than the corresponding 15S-hydroxy epimers.

In addition to not being specifically mentioned in the Belgian patent cited above, the 15-epi derivatives in this invention are important for their prostacyclin-like activity: in particular, the ability to inhibit platelet aggregation, to dissolve clots, to cause the coronary vessels to dilate, all with no undesirable side effects. However, for the natural prostacyclins (the 15S-derivatives), for example the compounds described in the above mentioned Belgian patent, this activity is always associated with a general vaso-dilatory effect which causes hypotension. It must be noted that the Belgian patent attributes no thrombolytic activity to the compounds it covers. However, the 15-epi-prostacyclin derivatives described by the present invention do not produce general vaso-dilatation and so have no hypotensive effect.

Due to this particular characteristic, the compounds covered by this invention are excellent anti-thrombotic and thrombolytic agents useful in the treatment of acute myocardial infarction.

A compound used to treat myocardial infarction must be absolutely free of negative effects on systemic pressure: there must be no vaso-dilatory and hypotensive effect. This undesirable side effect is characteristic of natural prostacyclins like the 15S-derivatives described in Belgian patent No. 851,122 but is not seen for the compounds covered by the present invention. In addition to dissolving thrombi and clots, these are selective vaso-dilators at the coronary level with no general hypotensive effect nor undesirable side effects like the stimulation of the gastro-intestinal tract.

In this regard, a comparison of 15-epi-d,l-PGI$_2$ with the analogous 15S-d,l-PGI$_2$, and of these compounds with PGI$_2$, PGE$_1$, 5,6α-dihydro-PGI$_2$ and ω-tetranor-16-m-CF$_3$-phenoxy-5,6α-dihydro-PGI$_2$ is of interest. The figure shows their inhibition of platelet aggregation (percent) induced by 2 μM ADP in platelet rich plasma: conc. in ng/ml PRP (Platelet rich plasma) (logarithmic scale) * from arachidonic acid biosynthesis.

Expressed as IC$_{50}$ ng/ml (50% platelets aggregation inhibiting concentration) their approximate activities are:

| | |
|---|---|
| PGI$_2$* and d,l-PGI$_2$ | ≅ 4.5 |
| PGE$_1$ | ≅ 30 |
| d,l-15-epi-PGE$_2$ | ≅ 330 |
| 5,6α-dihydro-PGI$_2$ | ≅ 400 |
| ω-tetranor-16-m-CF$_3$-phenoxy-5,6α-dihydro-PGI$_2$ | > 5000 |
| d,l-5,α-dihydro-15-epi-PGI$_2$ | not active |
| d,l-5,6β-dihydro-15-epi-PGI$_2$ | not active |

Another important characteristic of these new 15-epi prostacycline analogues is that they show practically no PGE-like activity in the gastro-intestinal tract. Unlike the analogous 15S-hydroxy-5,6α-dihydro-prostacyclins and their 15-epi derivatives (totally inactive in the preceding test), these new compounds induce no contractions in the rat colon or in stomachs strips.

With PGE$_2$ as standard (100), potency ratios are as follows:

| | rat colon | stomach strips |
|---|---|---|
| PGE$_2$ | 100 | 100 |
| PGI$_2$* | 0 | 20 |
| d,l-PGI$_2$ | 0 | 20 |
| 15-epi-d,l-PGI$_2$ | 0 | 1 |
| 5,6α-dihydro-PGI$_2$ | 2.76 | 1.86 |
| 5,6β-dihydro-PGI$_2$ | 2 | 0.80 |
| 16,16-dimethyl-17-oxa-5,6α-dihydro-PGI$_2$ | 0.72 | 0.41** |
| ω-tetranor-16-m-CF$_3$-phenoxy-5,6α-dihydro-PGI$_2$ | 2.8 | 0.91 |
| d,l-5,6α-dihydro-15-epi-PGI$_2$ | 0 | 0.20 |
| d,l-5,6β-dihydro-15-epi-PGI$_2$ | 0 | 0.05 |

**This compound shows weak platelet aggregant activity.

Of further importance is the effect of these 15-epi derivatives as a relaxant and dilatory for bovine coronary arteries. Once again, they compare favorably with the 5,6-dihydro-PGI$_2$ analogues (that is, with the 15S-hydroxy):

| | Dilation, bovine coronary artery | Contraction, bovine coronary artery |
|---|---|---|
| PGI$_2$* | 100 | 0 |
| d,l-PGI$_2$ | 100 | 0 |
| d,l-15-epi-PGI$_2$ | 1 | 0 |
| 5,6α-dihydro-PGI$_2$ | 0.28 | 0 |
| 5,6β-dihydro-PGI$_2$ | 0 | 0.34 |
| 15-epi-d,l-5,6α-dihydro-PGI$_2$ | 0 | 0 |
| 15-epi-d,l-5,6β-dihydro-PGI$_2$ | 0 | 0 |
| ω-tetranor-16-m-CF$_3$-phenoxy-5,6α-dihydro-PGI$_2$ | 0.11 | 0 |
| PGE$_2$ | 0 | 100 |

In all of these areas (platelet aggregation inhibition, coronary vessel dilation, absence or attenuation of undesirable side effects), the range of activity does not differ substantially from that of the natural product PGI$_2$; compared to which there is a foreseeable (for a 15-epi derivative) decrease in potency. Therefore, these new compounds are not of necessity preferred to the natural product, to the 5,6-dihydro analogues, e.g. 5,6α-dihydro-PGI$_2$, or to the tetranor derivative which is less active than the natural product, but more stable.

However, the innovative and new aspect of these new 15-epi compounds is revealed by testing them using Gryglewsky's technique (Abstract II Int. Symp. on Prostaglandins, Halle, 9/19-21/1977, page 3) on anesthetized and heparinized cats to determine their clot disaggregant capacity in vivo. In this test, a $PGI_2$ dose of 2.5 μg/kg i.v. blocks the platelet aggregation phenomenon; the 5,6α-dihydro-$PGI_2$ (a 15S-hydroxy derivative) dose showing equal activity is 250 μg/kg i.v. So, for equally active disaggregant doses, the hypotensive effect is approximately 25% higher than that of $PGI_2$. The ω-tetranor analogue is 15 times less active as an anti-aggregant, while d,l-15-epi-$PGI_2$ requires 125 μg/kg i.v. to give the same effect as the above dose of $PGI_2$.

| | |
|---|---|
| $PGI_2$ | 2.5 μg/kg |
| d,l-$PGI_2$ | 4-5 μg/kg |
| d,l-15-epi-$PGI_2$ | 125 μg/kg |
| 5,6α-dihydro-$PGI_2$ | 250 μg/kg |

However, in terms of the present invention it is important and relevant that unlike biosynthetic-origin $PGI_2$ (from arachidonic acid), d,l-$PGI_2$ and 5,6α-dihydro-$PGI_2$ (which are all prostacyclin-like compounds in that the disaggregant phenomenon is accompanied by hypotension) the 15-epi analogues, e.g. d,l-15-epi-$PGI_2$, have a moderate and prolonged hypertensive effect, making them ideal anti-thrombic agents for elective use in treating acute myocardial infarction. The 15-epi-13,14-dehydro-derivatives also show a similar spectrum of activity.

A tipical compound of this series is the 15-epe-13,14-dehydro-20-methyl-$PGI_2$.

When compared with $PGI_2$ it appears as a $PGI_2$ like compound completely deprived of the ability to contract the bovine coronary artery, the rat colon and the stomach strips, whereas its ability in relaxing the bovine coronary artery strips is approximately 15% of that of $PGI_2$.

In reversing the platelet aggregation induced by 2 μM ADP in rabbit platelet rich plasma and in cat heparinized blood the $IC_{50}$ values (ng/ml) for 15-epi-13,14-dehydro-20-methyl-$PGI_2$ are respectively 75 and 100 the corresponding values for $PGI_2$ being 3.9 and 1.

The titled compound 15-epi-13,14-dehydro-20-methyl-$PGI_2$ is also devoid of any systematic hypotensive effect. The compounds covered by this invention are prepared with a procedure based on the dehydrohalogenation of a compound of formula (II)

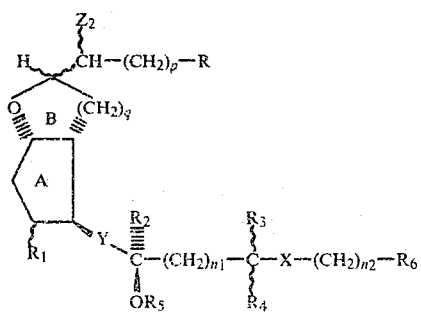

wherein R, p, q, $R_1$, Y, $R_2$, $R_5$, $n_1$, $R_3$, $R_4$, X, $n_2$ and $R_6$ are as defined above and $Z_2$ is a halogen atom, preferably chlorine, bromine or iodine and, if desired, the dehydrogenation product of formula (I) may be converted into another compound of formula (I), and/or, if desired, transformed to its salt, and/or, if desired, separated into its individual isomers.

The dehydrogenation is preferably run in an inert solvent with an appropriate dehyrohalogenating agent, and the solvent is preferably chosen from the group: dimethylsulfoxide, dimethylformamide, hexamethylphosphoramide, a linear or cyclic ether like dimethoxyethane, tetrahydrofuran, or dioxane, an aromatic hydrocarbon like benzene or toluene, liquid ammonia. These solvents may also be used in mixtures and at temperatures ranging from the liquefaction point of ammonia to the boiling point of water, although room temperature is particularly preferred.

The dehydrohalogenating agent is a base chosen preferably from: sodium dimethylsulfinyl carbanion, potassium dimethylsulfinyl carbonion, diazabicycloundecene, diazabicyclononene, and an alkaline metal amide or alcoholoate. The quantity of dehydrohalogenating base used in the reaction may vary from 1 to 5 moles per mole of compound, but the preferred ratio is from 1.5-1.8 moles of base per mole of compound (II).

As a function of the solvent, the temperature, the molar ratio of reagents and the nature of the halogenated substrate, the reaction time may range from 20-30 minutes to 3-4 days.

The reactivity of the halogenated substrate decreases from iodide to bromide to chloride.

Particularly preferred reaction conditions involve the use of diazabicycloundecene as dehydrohalogenating agent at room temperature in a solvent like dimethylformamide or dimethylsulfoxide. When the desired reaction product (I) has Y=—CH=$Z_1$—where $Z_1$ is halogen, these conditions allow selective dehydrohalogenation with no triple bond formation in position 13,14.

Satisfactory reaction conditions include the use of potassium alcoholate (preferably tert-butylate) or sodium or potassium dimethylsulfinyl carbanion in dimethylsulfoxide at room temperature, as well as that of an alkali or alkaline earth alcoholate in a low molecular weight anhydrous alcohol. In the latter case, as the base strength of the cation decreases, the quantity of base needed to effect dehydrohalogenation increases proportionately.

The dehydrohalogenation reaction normally gives a mixture of the E and Z isomers which may in turn be separated by fractional crystallization or column chromatography. Fractional crystallization from a solvent like ethyl ether or a hydrocarbon like n-pentane, n-hexane, or cyclohexane is preferred.

The optional transformation of a compound (I) into another formula (I), the formation of a salt of formula (I), and the separation of the mixture into individual isomers are run using standard procedures. However, the enol-ether structure of the compounds covered by this invention makes them very sensitive to acids, the optional transformation listed above must be effected under mild conditions, preferably neutral or basic.

In fact, acid medium catalyzes the addition of water across the exo-cyclic double bond to give hemi-acetal (III) from compound (I). (III) is in turn in equilibrium with hydroxyketone (IV),

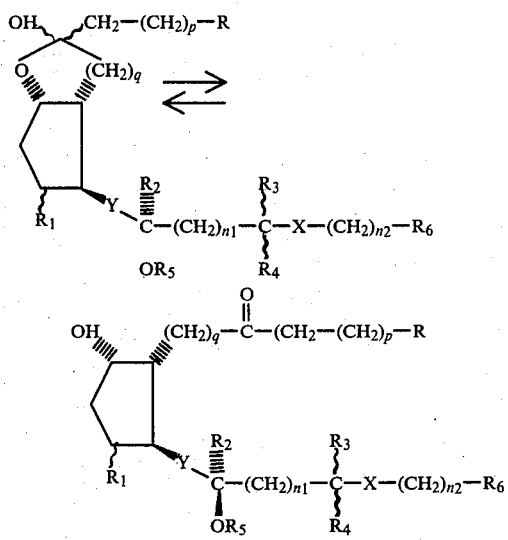

wherein the substituents are as defined above.

When the enol ether in (I) is too acid-sensitive, the desired transformations may be run on the starting material, compound (II).

For instance, a compound of formula (I) or, preferably, a compound of formula (II), wherein R is —COOH gives one of formula (I) or (II) wherein R is —CH$_2$OH upon reduction of the acid or its ester (prepared perhaps by reaction with an aliphatic alcohol in the presence of an acid catalyst like p-toluenesulfonic acid) with LiAlH$_4$ in diethyl ether or tetrahydrofurn at reflux. Or compounds wherein R is —COOH can give derivatives wherein R is

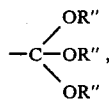

upon reaction of the hydrochloride of the carboximidic ester of the acid with an appropriate alcohol, as described for instance in J. Amer. Chem. Soc., 64, 1827 (1942). When R in the compounds of formula (I) or, preferably, in the compounds of formula (II), is —COOH, a derivative in which R is

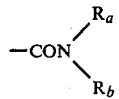

wherein R$_a$ and R$_b$ are as defined above, can be prepared, for instance, by treatment with an amine of formula NHR$_a$R$_b$ in the presence of a condensing agent like a carbodiimide, for example dicyclohexylcarbodiimide. Or, in the compounds of formula (I) or, preferably, in the compounds of formula (II), an R group of —COOH may be converted to R=—C=N by transforming the carboxyl to the corresponding acyl halide (preferably chloride), for instance by reaction with thionyl chloride in dioxane or dichloroethane at reflux, and then reacting the halide with ammonia to give the amide and dehydrating to give the nitrile. In turn, compounds of formula (I) or, preferably, of formula (II) with R=—C=N can give compounds of formula (I) or (II) wherein R is

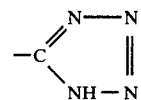

upon reaction with sodium azide and ammonium chloride in dimethylformamide, at temperatures ranging from room temperature to approximately 100° C.

When R$_1$ is hydroxy in compounds of formula (I) or (II), this can be converted to C$_1$–C$_6$ alkoxy or aryl-C$_1$–C$_6$-alkoxy with common etherification procedures like reaction with an optionally aryl substituted diazoalkane in the presence of an acid catalyst (for instance fluoroboric acid or boron trifluoride) in an organic solvent like dichloromethane. Another alternative is the reaction of the hydroxyl (free or as a salt) with an alkyl or arylalkyl halide in the presence of a base like Ag$_2$O in a solvent like dimethylsulfoxide or dimethylformamide.

Following the same procedure, a compound (I) or (II) in which R$_5$ is hydrogen gives the corresponding (I) or (II) where R$_5$ is C$_1$–C$_6$ alkyl or aryl-C$_1$–C$_6$-alkyl.

A compound of formula (I) in which R$_1$ is hydroxy may be transformed to one in which R$_1$ is acyloxy by using conventional methods, for instance treatment with an anhydride or halide (like the chloride of an appropriate carboxylic acid) in the presence of a base.

In order to selectively etherify or esterify only one of several free hydroxyl groups in a molecule (for instance, in transforming compound (I) or (II) where R$_1$ is —OH and R$_5$ is hydrogen into the derivative in which R$_1$ is C$_1$–C$_6$alkoxy or acyloxy and R$_5$ is hydrogen, or into that in which R$_1$ is hydroxy and R$_5$ is C$_1$–C$_6$alkyl or aryl-C$_1$–C$_6$-alkyl), the hydroxyl function to be unchanged must be suitably protected before the reaction with a known protecting group, which is then removed at the end of the reaction.

These protecting groups, generally ethers, are ones which may be converted back to hydroxyl under mild reaction conditions: for example, acetal ethers, enol ethers and silyl ethers. Preferred protecting groups are:

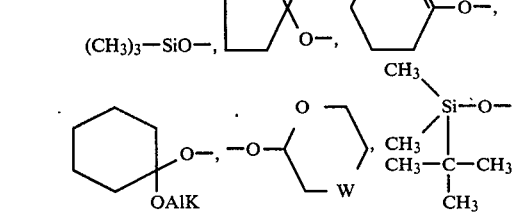

where W is —O— or —CH$_2$— and Alk is C$_1$–C$_6$alkyl.

Protecting groups may be removed from compounds of formula (II) with like acid hydrolysis: for example, with mono- or poly-carboxylic acids like formic, acetic, oxalic, citric, tartaric, in a solvent like water, acetone, tetrahydrofuran, dimethoxyethane, or a low molecular weight alcohol, or with a sulfonic acid like p-toluenesulfonic in a low molecular weight aliphatic alcohol like anhydrous methyl or ethyl, or with a polystyrene-sulfonate resin.

On the other hand, protecting groups must be removed from compounds of formula (I) under neutral conditions: for instance, with F⁻ ions in tetrahydrofuran when silyl ether groups are used.

If $R_1$ in compounds of formula (I) or (II) is an acyloxy group, it may be transformed to hydroxy by saponification with alkali, eliminating as much as possible prolonged contact with water for compounds (I).

A compound (I) or (II) in which Y is a $-CH=CZ_1-$ group where $Z_1$ is halogen may be converted into the derivative in which Y is a $-C\equiv C-$ group by dehydrohalogenation. This may be effected, for instance, by treatment with a dehydrohalogenating agent chosen from the group: dimethylsulfinyl carbanion ($CH_3SOCH_2^-$), diazabicycloundecene, diazabicyclononene, and an alkali metal amide or alcoholate in an inert solvent under reactions conditions similar to those described for transforming compound (II) into compound (I).

Salt formation for a compound (I) or (II) is done in the conventional manner, as is the optical separation of isomer mixtures: into optical antipodes, into diastereomers, or into geometric isomers. For example, optical antipodes may be separated from a racemic mixture by salt formation with optically active compounds; diastereomers may be separated through fractional crystallization or chromatography.

Fractional crystallizations are run in solvents like ethyl ether or an aliphatic hydrocarbon like n-pentane or n-hexane. Both preparative thin layer and column chromatography may be used, on silica gel or magnesium silicate with an eluent like dichloromethane, diethyl ether, isopropyl ether, ethyl acetate, benzene, methyl acetate or cyclohexane, as well as mixtures of them.

Diastereomers of compound (II) are preferably the only one separated by chromatography since the weakly acidic chromatographic support (silica gel or magnesium silicate) can catalyze the formation of compounds (III) and (IV) from enol ethers (I).

Compounds of formula (II) are prepared halocyclizing a compound of formula (V)

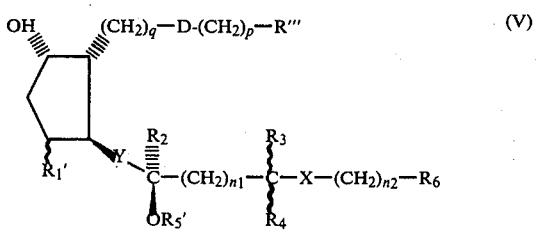

wherein p, q, Y, $R_2$, $n_1$, $R_3$, $R_4$, X, $n_2$ and $R_6$ are as defined above; D is a cis or trans double bond; R‴ is (a″) $-COOR'$ wherein R′ is as defined above; (b″) $-CH_2-R'^v$, wherein $R'^v$ is hydroxy or a known protecting group bound to $-CH_2-$ through an ether linkage;

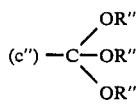

wherein each of R″ is as defined above;

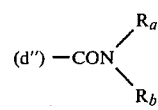

wherein $R_a$ and $R_b$ are as defined above;

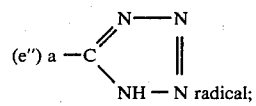 radical;

(f″) $-C\equiv N$; $R'_1$ is hydrogen, hydroxy, $C_1$-$C_6$ alkoxy, aryl-$C_1$-$C_6$-alkoxy, acyloxy or a known protectig group bound to the ring through an ether linkage; and $R'_5$ is hydrogen, $C_1$-$C_6$ alkyl, aryl-$C_1$-$C_6$-alkyl or the residue of a known protecting group as defined above and removing, by known methods, the protecting groups, when present.

The halocyclization may be run with a stoichiometric quality or a small excess of halogenating agent in an inert solvent, both with or without base. Preferred halogenating agents include iodine, bromine, chlorine, bromodioxane, bromopyridine, $Br_2$-pyridine-HBr, $KI_3$, pyrrolidonehydrotribromide, an N-haloamide like N-chlorosuccinimide, N-bromosuccinimide, N-iodosuccinimide, a copper halide like $CuCl_2$ or $CuBr_2$, a mixed halide like ICl or IBr, and mixtures of an alkali chloride with alkali chlorate, of alkali bromide with alkali bromate, or of alkali iodide with alkali iodate. Appropriate solvents include halogenated hydrocarbons like $CHCl_3$, $CCl_4$, $CH_2Cl_2$; aliphatic and cycloaliphatic hydrocarbons like n-hexane, n-heptane and cyclohexane; aromatic hydrocarbons like benzene, toluene and pyridine; cyclic or linear ethers like dioxane, tetrahydrofuran, diethyl ether, dimethoxyethane; as well as mixtures of them. However, the preferred solvents are halogenated hydrocarbons like $CH_2Cl_2$, since both compound (V) and the halogenating agent are usually soluble in these solvents.

When a hydrohalide acid forms during the halocyclization reaction, a stoichiometric quantity of a base must be present, either inorganic (like an oxide, carbonate or bicarbonate of an alkali or alkaline earth metal: e.g., CaO, $CaCO_3$, $K_2CO_3$) or organic (for instance, a tertiary amine like triethylamine, or an aromatic one like substituted or unsubstituted pyridine, or an anionic-type ion exchange resin).

The halocyclization may be run at temperatures ranging from $-70°$ C. to $100°$ C., although room temperature is preferred. The reaction time varies from a few minutes to several days, but is usually no more than two hours; often just a few minutes is sufficient.

When compound (V) contains other unsaturated bonds in addition to that represented by D, these may also suffer addition during the halocyclization. However, this addition product can easily be converted to the original unsaturation by treatment with an alkali or alkaline earth iodide in an appropriate solvent (like acetone) at a temperature varying from room temperature to reflux, although the former is preferred. Reaction time may run from 2–3 hours to 2–3 days.

Compounds (V) are known compounds and may be prepared as described in the following:

E. J. Corey et al., *Ann of New York Acad. of Sciences*, 180, 24(1971);

J. Fried et al., *J. Med. Chem.*, 16,429(1973);
G. L. Bundy et al., *J. Amer. Chem. Soc.*, 94,2124(1972);
Gandolfi et al., *Il Farmaco Ed. Sc.*, 27,1125(1972);
J. S. Bindra & R. Bindra, *Prostaglandins Synthesis*, New York(1977);
U.S. Pat. Nos. 3,935,254 and 4,041,064;
German Offenlegungsschrift No. 26 11 788 (Derwent-Farmdoc 61615 X);
German Offenlegungsschrift No. 26 10 503 (Derwent-Farmdoc 59715 X);
German Offenlegungsschrift No. 26 27 422 (Derwent-Farmdoc 85028 X);
German Offenlegungsschrift No. 23 22 673 (Derwent-Farmdoc 73279 U);
German Offenlegungsschrift No. 21 54 309 (Derwent-Farmdoc 31279 T);
German Offenlegungsschrift No. 24 40 919 (Derwent-Farmdoc 19594 W);
U.S. Pat. No. 3,706,789;
U.S. Pat. No. 3,728,382;
U.S. Pat. No. 3,903,131;
U.S. Pat. No. 3,962,293;
U.S. Pat. No. 3,969,380;
U.S. Pat. No. 3,890,372;
U.S. Pat. No. 3,636,120;
U.S. Pat. No. 3,883,513;
U.S. Pat. No. 3,932,389;
U.S. Pat. No. 3,932,479;
U.S. Pat. No. 4,021,477;
U.S. Pat. No. 4,029,681; and
British Pat. No. 1,483,880.

The compounds covered by this invention may be used in human or veterinary medicine when natural prostaglandins are therapeutically indicated, with the advantages of greatly reduced metabolism rates and of more selective therapeutic action.

For instance, these compounds are useful in treating ashma since they are strong broncodilators; to this end, they may be administered in many ways: orally (as tablets, capsules or pills; in drops or syrups); rectally (as suppositories); intravenously, intramuscularly, or subcutaneously; by inhalation (in an earosol or in vaporizer solutions); or by insufflation (as powder). Doses of approximately 0.01–4 mg/kg may be given from 1 to 4 times daily, with the exact dose depending on the age, weight and condition of the patient as well as the method of administration. For anti-ashmatic applications, the compounds covered by this invention may be given in combination with other anti-ashmatic agents: for instance, sympaticomimetics like isoproterenol, ephedrine, etc.; xanthine derivatives like theophylin and aminophylin; and corticosteroids like prednisolone and ACTH.

Furthermore, the compounds covered by this invention show oxytocic activity: that is, they may be used in place of oxytocin to induce labor or the expulsion of a dead fetus, in human as well as veterinary medicine. In this application the compounds are administered either by intravenous infusion at a dose of approximately 0.01 μg/kg/minute until labor is finished, or by mouth.

In addition, these compounds show luteolytic activity and are therefore useful for fertility control. In contrast to natural prostaglandins, they offer the advantage of a very reduced capacity to stimulate the smooth muscles, with a resultant lack of side effects like vomiting and diarrhea.

The pronounced antiulcerogenic effect of these compounds leads to their application in mammals to reduce and control excessive gastric excretion, and so to block the formation of gastrointestinal ulcers and to accelerate the cure of any ulcers already present. To this end, the compounds may be given by intravenous infusion or by intravenous, subcutaneous or intramuscular injection. In an infusion, the dose varies from approximately 0.1 μg to 500 μg per kilogram body weight per minute. The total daily dose, for both injection and infusion, is approximately 0.1–20 mg/kg, depending both on the patient's or animal'age, weight and condition and on the method of administration.

However, as discussed previously, the most important pharmacological activity of the compounds covered by this invention is their platelet anti-aggregant action: that is, their capacity to inhibit platelet aggregation by decreasing adhesiveness, to prevent the formation of thrombi and clots, and above all to dissolve already formed thrombi and clots in mammals. Further, they exhibit no hypotensive side effects.

The compounds may thus be used in preventing and treating both conditions of hyperlypidemia, like atherosclerosis and arteriosclerosis; and above all myocardial infarctions, since, as discussed above, the antithrombotic and thrombolytic activity of these compounds is not associated with any systemic hypotensive effect.

The above conditions may be treated with the normal methods of administration: that is, intravenously, subcutaneously, intramuscularly, etc., in doses ranging from 0.005 to 20 mg/kg/day, depending on the age, weight and condition of the patient as well as on the administration method. In emergency situations, intravenous administration is preferred.

Owing to their antithrombotic and thrombolytic activities which are no associated with any systemic hypotensive effect, the compounds of the invention can be used during haemodialysis and extracorporeal haemoperfusion in man.

So infusion of aqueous solutions of salts, e.g. alkaline salts, of 15-epi-prostacyclins in dosis equivalent to 30–150 ng/kg/min. in the dialyser inlet line and continued at the same rate throughout dialysis, reduces blood-artificial surface interaction and allow dialysis to be executed without thrombocytopenia and microembolization occurring. At present heparin is used during haemodialysis to prevent gloss clotting of blood. In spite of that, interaction between coagulation factors, blood cells and the artificial surfaces of the dialyser and lines occurs having thrombus deposition and intradialyser blood loss.

These events can be minimised, the dialyser efficiency prolonged and the systemic circulating disturbance prevented, in presence or not of haparin, by addition of 15-epi-prostacyclins.

The use of 15-epi-prostacyclins devoid of systemic hypotensive effect is certainly preferable to that of the natural hormon.

As discussed above, the compounds covered by this invention may be administered in many ways, depending on the application: intravenously, intramuscularly, subcutaneously, orally, endovaginally, rectally, topically.

Conventional excipients and carriers are used for the various pharmaceutical formulations. For oral administration, some examples are: lactose, dextrose, sucrose, mannitol, sorbitol, cellulose, talc, stearic acid, calcium or magnesium stearate, glycol, amides, gum arabic, gum adragant, alginic acid or alginates, lecithin, polysorbates, laurylsulfates, etc. For administration with a vaporizer, one uses a suspension or solution of the compound (preferably as a salt like the sodium derivative) in water. Alternatively, the pharmaceutical formulation may be a suspension or solution of the compound in a common liquified propellant like dichlorodifluoromethane or dichlorotetrafluoroethane to be administered from a pressurized container like an aerosol bomb. If the compound is not soluble in the propellant, a cosolvent may be added (like ethanol or dipropylenic clycol) and/or a tensio active substance. For parenteral administration, the compound may be dissolved, for example, in sterile water, in a lydocain hydrochloride or physiological saline solution, in a dextrose solution or in one of the other standard solvents used in this type of administration.

The following examples illustrate this invention without limiting it in any way.

EXAMPLE 1

A solution of 0.7 g of dl-9-deoxy-5-iodo-6βH-6,9α-oxide-11α,15R-dihydroxy-prost-13-trans-enoic acid methyl ester in 30 ml of methanol and 5 ml of water is treated for 6 hours at room temperature with 0.3 g of lithium hydroxide. After removal of the excess methanol, the aqueous solution is extracted with ethyl ether to remove any neutral impurities; it is then acidified to pH 5.2 and extracted repeatedly with freshly-distilled ethyl ether. The combined organic extract is dried and evaporated to give 0.675 g of dl-9-deoxy-5-iodo-6βH-6,9α-oxide-11α,15R-dihydroxy-prost-13-trans-enoic acid, which is dissolved in 10 ml of t-butanol and treated with 0.4 g of potassium t-butylate at 45° C. for 3 hours. The potassium iodide precipitate is separated by filtration, and the filtrate is evaporated to dryness to give a residue of 0.545 g of the potassium salt of dl-15-epi-PGI$_2$(C$_{20}$H$_{31}$O$_5$K, 390.55 g/mol). I.R. (KBr): $\nu_{max}$ = 1692 cm$^{-1}$

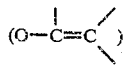

$^{13}$C N.M.R.: 182.5 (C-1); 158.1 (C-6); 139.8 and 134.3 (C 13-14); 100.5 (C-5); 87.0 (C-15); 80.6 and 75.6 (C 9-11); 58.1 (C-12); 49.0, 45.7, 42.5, 41.7, 37.6, 35.8 (C-18); 31.6 29.4, 26.6 (C-19); 18.3 (C-20) ppm from TMS in DMSO.

A sample of this (0.18 g) is dissolved in water (0.6 ml). The pH is then adjusted to 7.0 with 2 N sulfuric acid, 20% monobasic phosphate is added, and the mixture if held at pH 4.9 for 20 minutes. The aqueous solution is then extracted with ethyl acetate; the organic phase yields 0.058 g of dl-15-epi-6-keto-PGF$_{1\alpha}$.

Following the same procedure, nat- and ent-9-deoxy-5-iodo-6βH-6,9α-oxide-11α,15R-dihydroxy-prost-13-trans-enoic acid give, respectively:
nat-15-epi-PGI$_2$;
ent-15-epi-PGI$_2$.

EXAMPLE 2

A solution of 110 mg of dl-9-deoxy-5-iodo-6αH-6,9α-oxide-11α,15R-dihydroxy-prost-13-trans-enoic acid methyl ester is hydrolyzed following the procedure in the preceding example (3 ml methanol, 0.5 ml water, 30 mg LiOH) to give 98 mg of the free acid. 88.3 mg of this are dissolved in 2 ml of tert-butanol and treated at room temperature with 83 mg of potassium t-butylate. This is held for 5 hours at room temperature to effect complete dehydrohalogenation. Work-up of the mixture as in the preceding example gives 68 mg of the potassium salt of dl-15-epi-5E-PGI$_2$. I.R. (KBr): $\nu_{max}$ = 1692 cm$^{-1}$

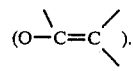

Similarly, from the single isomers, the following were obtained:
nat-15-epi-5E-PGI$_2$;
ent-15-epi-5E-PGI$_2$.

An aqueous solution of 80 mg of the potassium salt of dl-15-epi-5E-PGE$_2$ is brought to pH 4.8 with a saturated solution of monosodium phosphate and held for four hours at 30° C. Repeated extraction with ethyl acetate and evaporation of the organic phase give 51 mg of dl-6-keto-15-epi-PGF$_1$, identical in all respects with that prepared according to the preceding example.

EXAMPLE 3

1.2 g of 5-bromo-6αH-9-deoxy-6,9α-oxide-11α,15R-dihydroxy-prost-13-trans-enoic acid methyl ester in 18 ml of methanol is saponified by the addition of 0.18 g of lithium hydroxide in 1.8 ml of water. After 8 hours at room temperature, the solvent is evaporated and water is added. The aqueous solution is extracted with ethyl acetate and the extract discarded. The aqueous phase is acidified to pH 4.8 and extracted with 5:1 ethyl ether: methylene chloride. Drying and removal of solvent afford 1.08 g of the 5-bromo acid. A solution of this in 20 ml of tert-butanol is treated with 1.3 g of freshly sublimed potassium butylate. The reaction mixture is heated for 90 minutes at 50° C., cooled, separated from the KBr precipitate by filtration, and evaporated to give 0.9 g of the 15-epi-PGI$_2$ potassium salt. I.R. (KBr): $\nu_{max}$ = 1692 cm$^{-1}$

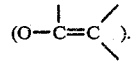

When treated as the enant-ester, the dl-bromo derivatives gave:
dl-15-epi-PGI$_2$;
ent-15-epi-PGI$_2$.

EXAMPLE 4

A solution of 0.4 g of 11,15-diepi-PGF$_{2\alpha}$-methyl ester in 8 ml of ethyl ether is emulsified with 12 ml of saturated sodium bicarbonate. With stirring and cooling to 0.2° C., a solution of iodine in ethyl ether is added (12.5 ml, I$_2$ concentration=25 mg/ml). Stirring is continued for another 8 hours, and the organic phase is separated and washed repeatedly with 0.1 N Na$_2$S$_2$O$_3$. Drying and removal of solvent give a residue which is purified on SiO$_2$ (ethyl ether as eluent) to give 340 mg of pure 6βH-5-iodo-11,15-diepe-5,6α-dihydro-PGI$_2$ methyl ester. 300 mg of this are reacted at room temperature with a solution of sodium methylate in anhydrous methanol prepared by dissolving 0.14 g of Na in 2.5 ml of MeOH. Complete dehydrohalogenation is achieved in 12 hours at room temperature to give 11,15-diepi-PGI$_2$-methyl ester. The reaction is followed by thin layer chromatography on silica gel and florisil, with ethyl acetate:triethylamine (100:2) as eluent. The methyl ester solution is then diluted with 1.5 ml of an aqueous solution of 1.0 N sodium hydroxide; hydrolysis is complete after 2 hours. Removal of the solvent affords a residue of the crude sodium salt of 11,15-diepi-PGI₂, to which a few drops of 1 N NaOH are added. After a few hours of refrigeration, a crystalline product separates which is collected by centrifugation to give 68 mg of pure nat-11,15-diepi-PGI₂ sodium salt. IR(KBr): $\nu_{max}=1692$ cm$^{-1}$

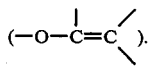

Ent-11,15-diepi-PGF₂α gives ent-11,15-diepi-PGI₂ sodium salt by the same procedure.

EXAMPLE 5

Following the procedure of example 4, one obtains 6βH-5-iodo-9-deoxy-6,9α-oxide-11α,15R-dihydroxy-20-methyl-prost-13-inoic acid methyl ester from 15-epi-5-cis-20-methyl-13,14-dehydro-PGF₂α methyl ester. 1 g of this product is stirred overnight under nitrogen with a sodium methylate solution prepared by dissolving 0.5 g of sodium in 7.5 ml of methanol. The resulting yellow solution is diluted with 5 ml of 1 N sodium hydroxide and the methyl ester of 20-methyl-15-epi-13,14-dehydro-PGI₂ is completely hydrolyzed after 4 hours. The methanol is removed under vacuum, and, upon cooling, the sodium salt precipitates from the aqueous solution. It is isolated by filtration and dried under vacuum to give 0.485 g of 20-methyl-15-epi-13,14-dehydro-PGI₂ sodium salt. $[\alpha]_D=+72.4$ (EtOH); IR (KBr): $\nu_{max}=1696$ cm$^{-1}$

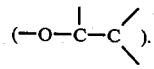

A 100 mg sample of this product dissolved in water, acidified with saturated monosodium phosphate and extracted gives 0.058 g of 20-methyl-15-epi-13,14-dehydro-6-keto-PGF₁α.

Proceeding analogously, 15-epi-13,14-dehydro-PGI₂ sodium salt was obtained.

EXAMPLE 6

0.3 g of 1,5-diazabycicloundecene is added to a solution of 0.5 g of 13t-5-iodo-6βH-6,9α-oxide-20-methyl-11α,15R-dihydroxy-prost-13-enoic acid methyl ester in 2.5 ml of anhydrous dimethylformamide; the resulting mixture is held at 60° C. for 8 hours. The solution is diluted with 10 ml of water and extracted repeatedly with 1:1 ethyl ether:pentane. The combined organic phase is washed with cold water, with cold 5.1 pH buffer, and then with water until neutral. After drying, removal of the solvent affords 0.32 g of 15-epi-20-methyl-PGI₂ methyl ester, I.R.(KBr): $\nu_{max}=1735$ cm$^{-1}$ (CO₂CH₃) and $\nu_{max}=1695$ cm$^{-1}$

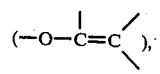

which is then saponified to give the sodium salt. From the analogous dl-5-iodo-dimethylamide derivative, the dl-15-epi-20-methyl-PGI₂ dimethylamide is prepared.

EXAMPLE 7

180 mg of potassium t-butylate is added to a solution of 250 mg of 13t-5,14-dibromo-6βH-6,9α-oxide-15R-methoxy-16S-methyl-prostenoic acid in 4.4 ml of dimethylsulfoxide; the resulting mixture is held for 4 hours under nitrogen with water excluded. The DMSO is removed under vacuum and the residue is taken up in 5:1 ethyl ether:dichloromethane and a 6.8 pH buffer while keeping the temperature at 0°-2° C. The combined organic phase is dried and evaporated (and the residue converted to its triethylamine salt) to give 0.105 g of 15R-methoxy-16S-methyl-11-deoxy-13,14-dehydro-PGI₂. I.R. (KBr): $\nu_{max}=1694$ cm$^{-1}$

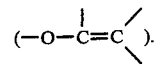

By the same procedure 15R-hydroxy-16S-methyl-11-deoxy-13,14-dehydro-PGI₂ was obtained.

EXAMPLE 8

A stirred solution of 2.5 g ($5.06\times10^{-3}$ mol) of dl-13t-20-methyl-5-iodo-6βH-6,9α-oxide-11α,15R-dihydroxy-prost-13-enoic acid in 12 ml of anhydrous methanol is treated at room temperature with 3 g of sodium methylate for 6 hours under nitrogen. The solvent is then evaporated and the dry residue taken up in 2 ml of 1 N NaOH; upon cooling, a crystalline product forms which is isolated by filtration to give the sodium salt of dl-20-methyl-15-epi-PGI₂. I.R. (KBr): $\nu_{max}=1690$ cm$^{-1}$

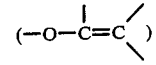

¹³C N.M.R.: 182.7 (C-1); 158.5 (C-6); 140.2 and 134.4 (C-13,14); 100.7 (C-5); 87.0 (C-15); 80.5 and 75.8 (C-9,11); 58.3 (C-12); 48.8, 45.8, 42.5, 41.8, 37.5, 35.7 (C-18); 31.6, 29.8, 29.2, 26.5 (C-19); 29.8, 28.2, 27.5, 24.2 (C-20); 18.3 (C-21) ppm from T.M.S. in DMSO-d₆.

In an analogous fashion, from the corresponding 5-iodo-6,9-oxides, the following compounds are prepared as their sodium salt (natural and d,l 15-epi):
20-methyl-15-epi-PGI₂;
20-ethyl-15-epi-PGI₂;
16S-methyl-15-epi-PGI₂;
16R-methyl-15-epi-PGI₂;
16S-fluoro-15-epi-PGI₂;
16R-fluoro-15-epi-PGI₂;
16(S,R)-fluoro-15-epi-PGI₂;
16S,20-dimethyl-15-epi-PGI₂;
16R,20-dimethyl-15-epi-PGI₂;
15-methyl-15-epi-PGI₂;
17-oxa-15-epi-PGI₂;
20 methyl-17-oxa-15-epi-PGI₂;
16,16-dimethyl-17-oxa-15-epi-PGI₂;
16,16-dimethyl-15-epi-PGI₂;
16,16,20-trimethyl-17-oxa-15-epi-PGI₂;
16,16-dimethyl-20-ethyl-17-oxa-15-epi-PGI₂;
ω-nor-19-cyclohexyl-15-epi-PGI₂;
ω-bisnor-18-cyclohexyl-15-epi-PGI₂;
ω-trinor-17-cyclohexyl-15-epi-PGI₂;
ω-trinor-16(S),(R)- and (S,R)-fluoro-17-cyclohexyl-15-epi-PGI₂;

ω-trinor-17l-phenyl-15-epi-PGI$_2$;
ω-trinor-17-cyclopentyl-15-epi-PGI$_2$;
ω-trinor-17-(2'-norbornyl)-15-epi-PGI$_2$;
ω-trinor-17-(2'-tetrahydrofuryl)-15-epi-PGI$_2$;
ω-trinor-17-(2'-furyl)-15-epi-PGI$_2$;
ω-tetranor-16-cyclohexyl-15-epi-PGI$_2$;
ω-tetranor-16-phenyl-15-epi-PGI$_2$;
ω-tetranor-16-phenoxy-15-epi-PGI$_2$;
ω-tetranor-16-p-fluorophenoxy-15-epi-PGI$_2$;
ω-tetranor-16-p-chlorophenoxy-15-epi-PGI$_2$;
ω-tetranor-16-m-chlorophenoxy-15-epi-PGI$_2$;
ω-tetranor-16-m-trifluoromethylphenoxy-15-epi-PGI$_2$;
ω-tetranor-16-(2'-norbornyl)-15-epi-PGI$_2$;
ω-tetranor-16-butoxy-15-epi-PGI$_2$;
ω-trinor-16-methyl-16-butoxy-15-epi-PGI$_2$;
ω-trinor-16-methyl-16-propoxy-15-epi-PGI$_2$;
ω-trinor-16-methyl-16-amyloxy-15-epi-PGI$_2$;
13,14-dihydro-20-methyl-15-epi-PGI$_2$;
13,14-dihydro-15-epi-PGI$_2$;
13,14-dihydro-20-ethyl-15-epi-PGI$_2$;
13,14-dihydro-16S-methyl-15-epi-PGI$_2$;
13,14-dihydro-16R-methyl-15-epi-PGI$_2$;
13,14-dihydro-15-methyl-15-epi-PGI$_2$;
13,14-dihydro-16,16-dimethyl-17-oxa-15-epi-PGI$_2$;
13,14-dihydro-16,16-dimethyl-15-epi-PGI$_2$;
13,14-dihydro-16,16,20-trimethyl-17-oxa-15-epi-PGI$_2$;
13,14-dihydro-16,16-dimethyl-20-ethyl-17-oxa-15-epi-PGI$_2$;
13,14-dihydro-ω-nor-19-cyclohexyl-15-epi-PGI$_2$;
13,14-dihydro-ω-bisnor-18-cyclohexyl-15-epi-PGI$_2$;
13,14-dihydro-ω-trinor-17-cyclohexyl-15-epi-PGI$_2$.
13,14-dihydro-ω-trinor-17-phenyl-15-epi-PGI$_2$;
13,14-dihydro-ω-trinor-17-cyclopentyl-15-epi-PGI$_2$;
13,14-dihydro-ω-trinor-17-(2'-norbornyl)-15-epi-PGI$_2$;
13,14-dihydro-ω-trinor-17-(2'-tetrahydrofuryl)-15-epi-PGI$_2$;
13,14-dihydro-ω-tetranor-16-cyclohexyl-15-epi-PGI$_2$;
13,14-dihydro-ω-tetranor-16-phenyl-15-epi-PGI$_2$;
13,14-dihydro-ω-tetranor-16-phenoxy-15-epi-PGI$_2$;
13,14-dihydro-ω-tetranor-16-p-fluorophenoxy-15-epi-PGI$_2$;
13,14-dihydro-ω-tetranor-16-m-chlorophenoxy-15-epi-PGI$_2$;
13,14-dihydro-ω-tetranor-16-m-trifluoromethylphenoxy-15-epi-PGI$_2$;
13,14-dehydro-15-epi-PGI$_2$;
13,14-dehydro-20-methyl-15-epi-PGI$_2$;
13,14-dehydro-20-ethyl-15-epi-PGI$_2$;
13,14-dehydro-16S-methyl-15-epi-PGI$_2$;
13,14-dehydro-16R-methyl-15-epi-PGI$_2$;
13,14-dehydro-16(S,R)-methyl-15-epi-PGI$_2$;
13,14-dehydro-16S,20-dimethyl-15-epi-PGI$_2$;
13,14-dehydro-15-methyl-15-epi-PGI$_2$;
13,14-dehydro-ω-nor-19-cyclohexyl-15-epi-PGI$_2$;
13,14-dehydro-ω-bisnor-18-cyclohexyl-15-epi-PGI$_2$;
13,14-dehydro-ω-trinor-17-cyclohexyl-15-epi-PGI$_2$;
13,14-dehydro-ω-trinor-16(S),(R)- and (S,R)-fluoro-17-cyclohexyl-15-epi-PGI$_2$;
13,14-dehydro-ω-trinor-17-phenyl-15-epi-PGI$_2$;
13,14-dehydro-ω-trinor-17-cyclopentyl-15-epi-PGI$_2$;
13,14-dehydro-ω-trinor-17-(2'-norbornyl)-15-epi-PGI$_2$;
13,14-dehydro-ω-trinor-17-(2'-tetrahydrofuryl)-15-epi-PGI$_2$;
13,14-dehydro-ω-tetranor-16-cyclohexyl-15-epi-PGI$_2$;
13,14-dehydro-ω-tetranor-16-phenyl-15-epi-PGI$_2$;
13,14-dehydro-ω-tetranor-16-phenoxy-15-epi-PGI$_2$;
13,14-dehydro-ω-tetranor-16-p-fluorophenoxy-15-epi-PGI$_2$;
13,14-dehydro-ω-tetranor-16-m-chlorophenoxy-15-epi-PGI$_2$;
13,14-dehydro-ω-tetranor-16-m-trifluoromethylphenoxy-15-epi-PGI$_2$;

as well as:
ent-20-methyl-15-epi-PGI$_2$;
ent-20-ethyl-15-epi-PGI$_2$;
ent-16S-methyl-15-epi-PGI$_2$;
ent-16R-methyl-15-epi-PGI$_2$;
ent-16S-fluoro-15-epi-PGI$_2$;
ent-16R-fluoro-15-epi-PGI$_2$;
ent-16(S,R)-fluoro-15-epi-PGI$_2$;
ent-16S,20-dimethyl-15-epi-PGI$_2$;
ent-16R,20-dimethyl-15-epi-PGI$_2$;
ent-15-methyl-15-epi-PGI$_2$;
ent-17-oxa-15-epi-PGI$_2$;
ent-20-methyl-17-oxa-15-epi-PGI$_2$;
ent-16,16-dimethyl-17-oxa-15-epi-PGI$_2$;
ent-16,16-dimethyl-15-epi-PGI$_2$;
ent-16,16,20-trimethyl-17-oxa-15-epi-PGI$_2$;
ent-16,16-dimethyl-20-ethyl-17-oxa-15-epi-PGI$_2$;
ent-ω-nor-19-cyclohexyl-15-epi-PGI$_2$;
ent-ω-bisnor-18-cyclohexyl-15-epi-PGI$_2$;
ent-ω-trinor-17-cyclohexyl-15-epi-PGI$_2$;
ent-ω-trinor-16(S),(R)- and (S,R)-fluoro-17-cyclohexyl-15-epi-PGI$_2$;
ent-ω-trinor-17-phenyl-15-epi-PGI$_2$;
ent-ω-trinor-17-cyclopentyl-15-epi-PGI$_2$;
ent-ω-trinor-17-(2'-norbornyl)-15-epi-PGI$_2$;
ent-ω-trinor-17-(2'-tetrahydrofuryl)-15-epi-PGI$_2$;
ent-ω-trinor-17-(2'-furyl)-15-epi-PGI$_2$;
ent-ω-tetranor-16-cyclohexyl-15-epi-PGI$_2$;
ent-ω-tetranor-16-phenyl-15-epi-PGI$_2$;
ent-ω-tetranor-16-phenoxy-15-epi-PGI$_2$;
ent-ω-tetranor-16-p-fluorophenoxy-15-epi-PGI$_2$;
ent-ω-tetranor-16-p-chlorophenoxy-15-epi-PGI$_2$;
ent-ω-tetranor-16-m-chlorophenoxy-15-epi-PGI$_2$;
ent-ω-tetranor-16-m-trifluoromethylphenoxy-15-epi-PGI$_2$;
ent-ω-tetranor-16-(2'-norbornyl)-15-epi-PGI$_2$;
ent-ω-tetranor-16-butoxy-15-epi-PGI$_2$;
ent-ω-trinor-16-methyl-16-butoxy-15-epi-PGI$_2$;
ent-ω-trinor-16-methyl-16-propoxy-15-epi-PGI$_2$;
ent-ω-trinor-16-methyl-16-amyloxy-15-epi-PGI$_2$;
13,14-dihydro-ent-20-methyl-15-epi-PGI$_2$;
13,14-dihydro-ent-15-epi-PGI$_2$;
13,14-dihydro-ent-20-ethyl-15-epi-PGI$_2$;
13,14-dihydro-ent-16S-methyl-15-epi-PGI$_2$;
13,14-dihydro-ent-16R-methyl-15-epi-PGI$_2$;
13,14-dihydro-ent-15-methyl-15-epi-PGI$_2$;
13,14-dihydro-ent-16,16-dimethyl-17-oxa-15-epi-PGI$_2$;
13,14-dihydro-ent-16,16-dimethyl-15-epi-PGI$_2$;
13,14-dihydro-ent-16,16,20-trimethyl-17-oxa-15-epi-PGI$_2$;
13,14-dihydro-ent-16,16-dimethyl-20-ethyl-17-oxa-15-epi-PGI$_2$;
13,14-dihydro-ent-ω-nor-19-cyclohexyl-15-epi-PGI$_2$;
13,14-dihydro-ent-ω-bisnor-18-cyclohexyl-15-epi-PGI$_2$;
13,14-dihydro-ent-ω-trinor-17-cyclohexyl-15-epi-PGI$_2$.
13,14-dihydro-ent-ω-trinor-17-phenyl-15-epi-PGI$_2$;
13,14-dihydro-ent-ω-trinor-17-cyclopentyl-15-epi-PGI$_2$;
13,14-dihydro-ent-ω-trinor-17-(2'-norbornyl)-15-epi-PGI$_2$,
13,14-dihydro-ent-ω-trinor-17-(2'-tetrahydrofuryl)-15-epi-PGI$_2$;
13,14-dihydro-ent-ω-tetranor-16-cyclohexyl-15-epi-PGI$_2$;

13,14-dihydro-ent-ω-tetranor-16-phenyl-15-epi-PGI$_2$;
13,14-dihydro-ent-ω-tetranor-16-phenoxy-15-epi-PGI$_2$;
13,14-dihydro-ent-ω-tetranor-16-p-fluorophenoxy-15-epi-PGI$_2$;
13,14-dihydro-ent-ω-tetranor-16-m-chlorophenoxy-15-epi-PGI$_2$;
13,14-dihydro-ent-ω-tetranor-16-m-trifluoromethylphenoxy-15-epi-PGI$_2$;
13,14-dehydro-ent-15-epi-PGI$_2$;
13,14-dehydro-ent-20-methyl-15-epi-PGI$_2$;
13,14-dehydro-ent-20-ethyl-15-epi-PGI$_2$;
13,14-dehydro-ent-16S-methyl-15-epi-PGI$_2$;
13,14-dehydro-ent-16R-methyl-15-epi-PGI$_2$;
13,14-dehydro-ent-16(S,R)-methyl-15-epi-PGI$_2$;
13,14-dehydro-ent-16S,20-dimethyl-15-epi-PGI$_2$;
13,14-dehydro-ent-15-methyl-15-epi-PGI$_2$;
13,14-dehydro-ent-ω-nor-19-cyclohexyl-15-epi-PGI$_2$;
13,14-dehydro-ent-ω-bisnor-18-cyclohexyl-15-epi-PGI$_2$;
13,14-dehydro-ent-ω-trinor-17-cyclohexyl-15-epi-PGI$_2$;
13,14-dehydro-ent-ω-trinor-16(S),(R)- and (S,R)-fluoro-17-cyclohexyl-15-epi-PGI$_2$;
13,14-dehydro-ent-ω-trinor-17-phenyl-15-epi-PGI$_2$;
13,14-dehydro-ent-ω-trinor-17-cyclopentyl-15-epi-PGI$_2$;
13,14-dehydro-ent-ω-trinor-17-(2′-norbornyl)-15-epi-PGI$_2$;
13,14-dehydro-ent-ω-trinor-17-(2′-tetrahydrofuryl)-15-epi-PGI$_2$;
13,14-dehydro-ent-ω-tetranor-16-cyclohexyl-15-epi-PGI$_2$;
13,14-dehydro-ent-ω-tetranor-16-phenyl-15-epi-PGI$_2$;
13,14-dehydro-ent-ω-tetranor-16-phenoxy-15-epi-PGI$_2$;
13,14-dehydro-ent-ω-tetranor-16-p-fluorophenoxy-15-epi-PGI$_2$;
13,14-dehydro-ent-ω-tetranor-16-m-chlorophenoxy-15-epi-PGI$_2$;
13,14-dehydro-ent-ω-tetranor-16-m-trifluoromethylphenoxy-15-epi-PGI$_2$;
20-methyl-11,15-diepi-PGI$_2$;
20-ethyl-11,15-diepi-PGI$_2$;
16S-methyl-11,15-diepi-PGI$_2$;
16R-methyl-11,15-diepi-PGI$_2$;
16S-fluoro-11,15-diepi-PGI$_2$;
16R-fluoro-11,15-diepi-PGI$_2$;
16(S,R)-fluoro-11,15-diepi-PGI$_2$;
16S,20-dimethyl-11,15-diepi-PGI$_2$;
16R,20-dimethyl-11,15-diepi-PGI$_2$;
15-methyl-11,15-diepi-PGI$_2$;
17-oxa-11,15-diepi-PGI$_2$;
20 methyl-17-oxa-11,15-diepi-PGI$_2$;
16,16-dimethyl-17-oxa-11,15-diepi-PGI$_2$;
16,16-dimethyl-11,15-diepi-PGI$_2$;
16,16,20-trimethyl-17-oxa-11,15-diepi-PGI$_2$;
16,16-dimethyl-20-ethyl-17-oxa-11,15-diepi-PGI$_2$;
ω-nor-19-cyclohexyl-11,15-diepi-PGI$_2$;
ω-bisnor-18-cyclohexyl-11,15-diepi-PGI$_2$;
ω-trinor-17-cyclohexyl-11,15-diepi-PGI$_2$;
ω-trinor-16(S),(R)- and (S,R)-fluoro-17-cyclohexyl-11,15-diepi-PGI$_2$;
ω-trinor-17-phenyl-11,15-diepi-PGI$_2$;
ω-trinor-17-cyclopentyl-11,15-diepi-PGI$_2$;
ω-trinor-17-(2′-norbornyl)-11,15-diepi-PGI$_2$;
ω-trinor-17-(2′-tetrahydrofuryl)-11,15-diepi-PGI$_2$;
ω-trinor-17-(2′-furyl)-11,15-diepi-PGI$_2$;
ω-tetranor-16-cyclohexyl-11,15-diepi-PGI$_2$;
ω-tetranor-16-phenyl-11,15-diepi-PGI$_2$;
ω-tetranor-16-phenoxy-11,15-diepi-PGI$_2$;
ω-tetranor-16-p-fluorophenoxy-11,15-diepi-PGI$_2$;
ω-tetranor-16-p-chlorophenoxy-11,15-diepi-PGI$_2$;
ω-tetranor-16-m-chlorophenoxy-11,15-diepi-PGI$_2$;
ω-tetranor-16-m-trifluoromethylphenoxy-11,15-diepi-PGI$_2$;
ω-tetranor-16-(2′-norbornyl)-11,15-diepi-PGI$_2$;
ω-tetranor-16-butoxy-11,15-diepi-PGI$_2$;
ω-trinor-16-methyl-16-butoxy-11,15-diepi-PGI$_2$;
ω-trinor-16-methyl-16-propoxy-11,15-diepi-PGI$_2$;
ω-trinor-16-methyl-16-amyloxy-11,15-diepi-PGI$_2$;
13,14-dihydro-20-methyl-11,15-diepi-PGI$_2$;
13,14-dihydro-11,15-diepi-PGI$_2$;
13,14-dihydro-20-ethyl-11,15-diepi-PGI$_2$;
13,14-dihydro-16S-methyl-11,15-diepi-PGI$_2$;
13,14-dihydro-16R-methyl-11,15-diepi-PGI$_2$;
13,14-dihydro-15-methyl-11,15-diepi-PGI$_2$;
13,14-dihydro-16,16-dimethyl-17-oxa-11,15-diepi-PGI$_2$;
13,14-dihydro-16,16-dimethyl-11,15-diepi-PGI$_2$;
13,14-dihydro-16,16,20-trimethyl-17-oxa-11,15-diepi-PGI$_2$;
13,14-dihydro-16,16-dimethyl-20-ethyl-17-oxa-11,15-diepi-PGI$_2$;
13,14-dihydro-ω-nor-19-cyclohexyl-11,15-diepi-PGI$_2$;
13,14-dihydro-ω-bisnor-18-cyclohexyl-11,15-diepi-PGI$_2$;
13,14-dihydro-ω-trinor-17-cyclohexyl-11,15-diepi-PGI$_2$;
13,14-dihydro-ω-trinor-17-phenyl-11,15-diepi-PGI$_2$;
13,14-dihydro-ω-trinor-17-cyclopentyl-11,15-diepi-PGI$_2$;
13,14-dihydro-107 -trinor-17-(2′-norbornyl)-11,15-diepi-PGI$_2$;
13,14-dihydro-ω-trinor-17-(2′-tetrahydrofuryl)-11,15-diepi-PGI$_2$;
13,14-dihydro-ω-tetranor-16-cyclohexyl-11,15-diepi-PGI$_2$;
13,14-dihydro-ω-tetranor-16-phenyl-11,15-diepi-PGI$_2$;
13,14-dihydro-ω-tetranor-16-phenoxy-11,15-diepi-PGI$_2$;
13,14-dihydro-ω-tetranor-16-p-fluorophenoxy-11,15-diepi-PGI$_2$;
13,14-dihydro-ω-tetranor-16-m-chlorophenoxy-11,15-diepi-PGI$_2$;
13,14-dihydro-ω-tetranor-16-m-trifluoromethylphenoxy-11,15-diepi-PGI$_2$;
13,14-dehydro-11,15-diepi-PGI$_2$;
13,14-dehydro-20-methyl-11,15-diepi-PGI$_2$;
13,14-dehydro-20-ethyl-11,15-diepi-PGI$_2$;
13,14-dehydro-16S-methyl-11,15-diepi-PGI$_2$;
13,14-dehydro-16R-methyl-11,15-diepi-PGI$_2$;
13,14-dehydro-16(S,R)-methyl-11,15-diepi-PGI$_2$;
13,14-dehydro-16S,20-dimethyl-11,15-diepi-PGI$_2$;
13,14-dehydro-15-methyl-11,15-diepi-PGI$_2$;
13,14-dehydro-ω-nor-19-cyclohexyl-11,15-diepi-PGI$_2$;
13,14-dehydro-ω-bisnor-18-cyclohexyl-11,15-diepi-PGI$_2$;
13,14-dehydro-ω-trinor-17-cyclohexyl-11,15-diepi-PGI$_2$;
13,14-dehydro-ω-trinor-16(S),(R)- and (S,R)-fluoro-17-cyclohexyl-11,15-diepi-PGI$_2$;
13,14-dehydro-ω-trinor-17-phenyl-11,15-diepi-PGI$_2$;
13,14-dehydro-ω-trinor-17-cyclopentyl-11,15-diepi-PGI$_2$;
13,14-dehydro-ω-trinor-17-(2′-norbornyl)-11,15-diepi-PGI$_2$;
13,14-dehydro-ω-trinor-17-(2′-tetrahydrofuryl)-11,15-diepi-PGI$_2$;

13,14-dehydro-ω-tetranor-16-cyclohexyl-11,15-diepi-PGI$_2$;

13,14-dehydro-ω-tetranor-16-phenyl-11,15-diepi-PGI$_2$;

13,14-dehydro-ω-tetranor 16-phenoxy-11,15-diepi-PGI$_2$;

13,14-dehydro-ω-tetranor-16-p-fluorophenoxy-11,15-diepi-PGI$_2$;

13,14-dehydro-ω-tetranor-16-m-chlorophenoxy-11,15-diepi-PGI$_2$;

13,14-dehydro-ω-tetranor-16-m-trifluoromethyl-phenoxy-11,15-diepi-PGI$_2$.

EXAMPLE 9

0.55 g of freshly sublimed potassium t-butylate is added to a solution of 0.8 g of 5-chloro-6βH-6,9α-oxide-15R-hydroxy-prost-13-enoic acid in 6.5 ml of dimethylsulfoxide. After 24 hours in an inert atmosphere, the DMSO is evaporated and the residue is partitioned between ethyl ether:pentane and a pH 6.8 buffer. The organic phase is dried and evaporated to give 0.52 g of 11-deoxy-15-epi-PGI$_2$, which is stored as its triethylamine salt. I.R. (KBr): $\nu_{max}$=1697 cm$^{-1}$

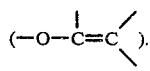

Proceeding analogously, the following compounds were prepared:

11-deoxy-16S-methyl-15-epi-PGI$_2$;
11-deoxy-16,16-dimethyl-15-epi-PGI$_2$;
11-deoxy-16,16,20-trimethyl-17-oxa-15-epi-PGI$_2$;
11-deoxy-16,16-dimethyl-20-ethyl-17-oxa-15-epi-PGI$_2$.

EXAMPLE 10

280 mg of sodium t-butylate is added to a solution of 461 mg of 13t-16S,20-dimethyl-5-bromo-6βH-6,9α-oxide-15-epi-prost-13-trans-enoic acid in 9 ml of anhydrous tert-butanol; the resulting mixture is held at 40°–45° C. for 10 hours. After cooling, the solvent is evaporated under vacuum to give the sodium salt of 16S-20-dimethyl-15-epi-PGI$_2$ (sodium butylate and sodium bromide mixture). Crystalliwation from 2 N sodium hydrate gives 0.21 g of pure product. I.R. (KBr): $\nu_{max}$=1690 cm$^{-1}$

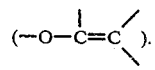

In an analogous fashion, all of the compounds listed in example 8 were prepared from the 5-bromo-6βH-6,9α-oxides.

We claim:

1. A 15-epi compound of the formula

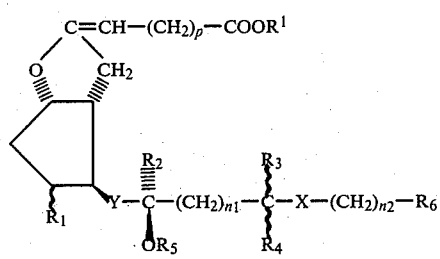

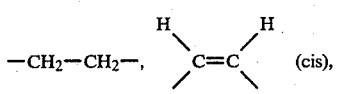

wherein
R$^1$ is hydrogen or C$_1$–C$_6$ alkyl;
p is zero or an integer of 1–7;
R$_1$ is hydroxy, C$_1$–C$_6$ alkoxy, benzyloxy, or acyloxy;
Y is chosen from the group:

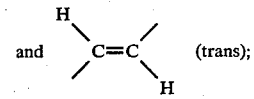

R$_2$ is hydrogen, C$_1$–C$_6$ alkyl or C$_2$–C$_6$ alkenyl;
R$_5$ is hydrogen or C$_1$–C$_6$ alkyl;
n$_1$ and n$_2$, whether the same or different, are zero or an integer of 1 to 6,;
R$_3$ and R$_4$, whether the same or different, are hydrogen, C$_1$–C$_6$ alkyl or may form a

group with a carbon atom to which they are bound;
X is chosen from —O— or —S—;
R$_6$ is a substituent chosen from (a) C$_1$–C$_4$ alkyl, (b) a C$_3$–C$_9$ cycloalkyl, C$_3$–C$_9$ cycloalkenyl, norbornyl, or adamantyl radical each of which radicals may be substituted by one or more C$_1$–C$_6$ alkyl or C$_1$–C$_6$-alkoxy groups;
and a pharmaceutically or veterinarily acceptable salt thereof.

2. Compound of claim 1, wherein Y is cis- or trans—CH=CH—.

3. Compound of claim 1, wherein p is an integer of 1 to 5; Y is trans—CH=CH—; R$_1$ is hydroxy; R$_2$ is hydrogen or C$_1$–C$_6$ alkyl; n$_1$ and n$_2$ are independently zero or an integer of 1 to 3; R$_3$ and R$_4$ are independently hydrogen or C$_1$–C$_6$ alkyl; X is —O—; R$_6$ is C$_1$–C$_4$ alkyl or C$_3$–C$_9$ cycloalkyl or C$_3$–C$_9$ cycloalkenyl optionally substituted with one or more C$_1$–C$_6$ alkyl or C$_1$–C$_6$ alkoxy groups.

4. A compound selected from the group consisting of:
15-epi-17-oxa-PGI$_2$;
15-epi-17-oxa-20-methyl-PGI$_2$;
15-epi-17-trinor-16-methyl-16-butoxy-PGI$_2$;
15-epi-17-trinor-16-methyl-16-propoxy-PGI$_2$;
15-epi-17-trinor-16-methyl-16-amyloxy-PGI$_2$;
15-epi-16-tetranor-16-butoxy-PGI$_2$;
and a pharmaceutically or veterinarily acceptable salt thereof.

5. Compound of claim 1, wherein p is an integer between 1 and 5; $R_1$ is hydroxy; Y is trans—CH=CH—; $R_2$ is hydrogen or $C_1$-$C_6$ alkyl; $R_5$ is hydrogen or $C_1$-$C_6$ alkyl; $n_1$ is zero or 1; $R_3$ and $R_4$ are independently hydrogen or methyl; X is —O—, $n_2$ is zero or an integer of 1 to 3; $R_6$ is $C_1$-$C_4$ alkyl.

6. Compound of claim 5, wherein p is 3.

7. Method of inhibiting platelet aggregation in a patient in need of such inhibition, said method comprising administering to said patient a therapeutically effective amount of a compound of claim 1.

8. Method of claim 7, wherein said amount is an amount of from about 0.005 to about 20 mg/kg/day.

9. Method of dissolving previously formed thrombi and clots in a mammal, said method comprising administering to said mammal a therapeutically effective amount of a compound of claim 1.

10. Method of claim 9, wherein said amount is an amount of from about 0.005 to about 20 mg/kg/day.

11. A thrombi- and clot-dissolving composition containing a thrombi- and clot-dissolving amount of the compound of claim 1 and a pharmaceutically or veterinarily acceptable carrier or diluent.

12. A platelet aggregation inhibiting composition containing a platelet aggregation inhibiting amount of a compound of claim 1 and a pharmaceutically or veterinarily acceptable carrier or diluent.

* * * * *